(12) United States Patent
Suri et al.

(10) Patent No.: US 7,563,911 B2
(45) Date of Patent: Jul. 21, 2009

(54) PROCESS FOR THE PREPARATION OF AMORPHOUS ATORVASTIN CALCIUM SALT (2:1)

(75) Inventors: Sanjay Suri, New Delhi (IN); Jujhar Singh, New Delhi (IN); Gurdeep Singh Sarin, New Delhi (IN); Baldev Raj Bansal, New Delhi (IN)

(73) Assignee: Morepen Laboratories Ltd., Himachal Pradesh (IN)

( * ) Notice: Subject to any disclaimer, the term of this patent is extended or adjusted under 35 U.S.C. 154(b) by 557 days.

(21) Appl. No.: 10/488,411

(22) PCT Filed: Aug. 31, 2001

(86) PCT No.: PCT/IN01/00152

§ 371 (c)(1),
(2), (4) Date: Sep. 30, 2004

(87) PCT Pub. No.: WO03/018547

PCT Pub. Date: Mar. 6, 2003

(65) Prior Publication Data

US 2005/0119493 A1    Jun. 2, 2005

(51) Int. Cl.
*C07D 207/30* (2006.01)
(52) U.S. Cl. .................................................. 548/537
(58) Field of Classification Search .................. 548/537
See application file for complete search history.

(56) References Cited

U.S. PATENT DOCUMENTS

| | | |
|---|---|---|
| 4,681,893 A | 7/1987 | Roth |
| 5,003,080 A | 3/1991 | Butler |
| 5,007,080 A | 4/1991 | Millan |
| 5,097,045 A | 3/1992 | Butler |
| 5,103,024 A | 4/1992 | Millar |
| 5,124,482 A | 6/1992 | Butler |
| 5,149,837 A | 9/1992 | Butler |
| 5,155,251 A | 10/1992 | Butler |
| 5,216,174 A | 6/1993 | Butler |
| 5,248,793 A | 9/1993 | Millar |
| 5,273,995 A | 12/1993 | Roth |
| 5,280,132 A | 1/1994 | Clarey |
| 5,342,952 A | 8/1994 | Butler |

FOREIGN PATENT DOCUMENTS

| | | |
|---|---|---|
| WO | 97/03960 A1 | 2/1997 |
| WO | 97/33959 A1 | 9/1997 |
| WO | 00/71116 A1 | 11/2000 |

*Primary Examiner*—James O Wilson
*Assistant Examiner*—Ebenezer Sackey
(74) *Attorney, Agent, or Firm*—Reed Smith LLP; Nanda P.B.A. Kumar

(57) ABSTRACT

Improved process for the preparation of amorphous atorvastatin calcium salt (2:1) comprises hydrolyzing the lactone form of atorvastatin of formula of FIG. 1 with aqueous alkali or alkaline earth metal base, extracting with organic solvent the reaction mixture and adding the same to an anti-solvent to precipitate the product and finally filtering the product to afford amorphous atorvastatin calcium (2:1). The process also comprises the preparation of amorphous atorvastatin calcium salt (2:1) from its crystalline form.

4 Claims, 3 Drawing Sheets

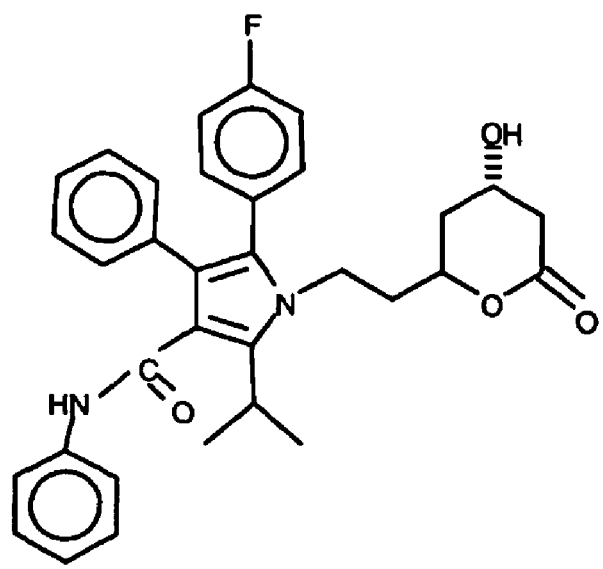
*Figure: 1.*
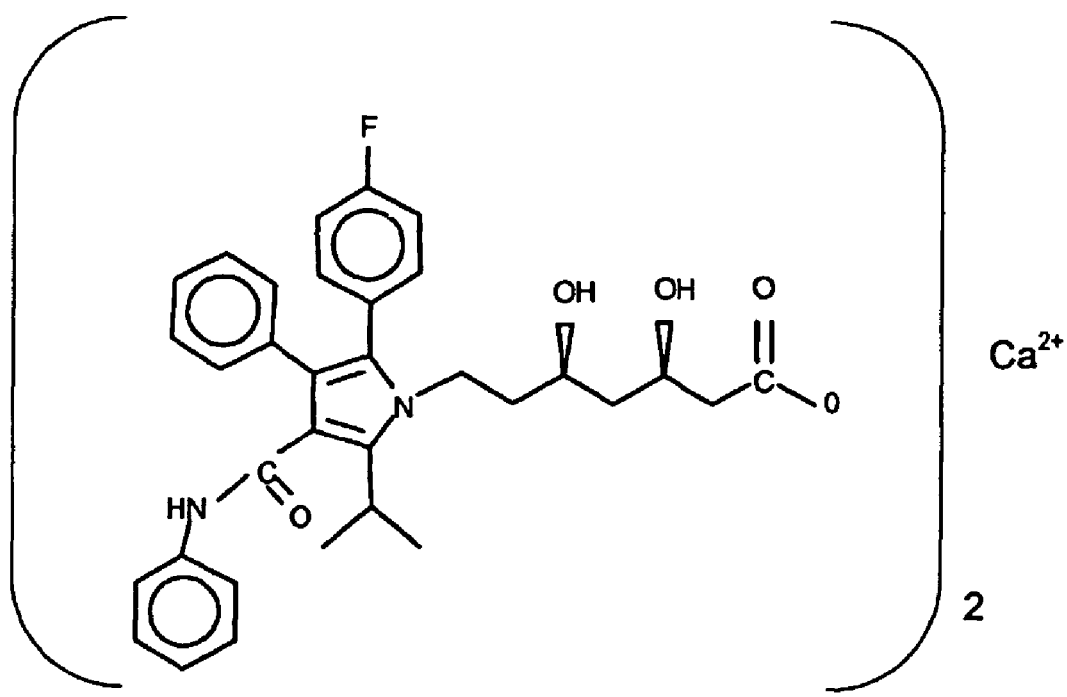
*Figure: 2.*

PROCESS FOR THE PREPARATION OF AMORPHOUS ATORVASTIN CALCIUM SALT (2:1)

The invention relates to an improved process for the preparation of amorphous atorvastatin calcium salt (2:1). It is chemically known as [R—(R*,R*)]-2-(4-fluorophenyl)-β,δ-dihydroxy-5-(1-methylethyl)-3-phenyl4-[(phenylamino)carbonyl]-1H-pyrrole-1-heptanoic acid hemicalcium salt. This drug is a synthetic HMG-COA reductase inhibitor which is used for the treatment of hyperlipidemia and hypocholesterolemia.

The accompanying drawings show as follows:

FIG. 1 shows the formula of (2R-trans)-5-(4-Fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

FIG. 2 shows the formula of [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1).

Figure 3:
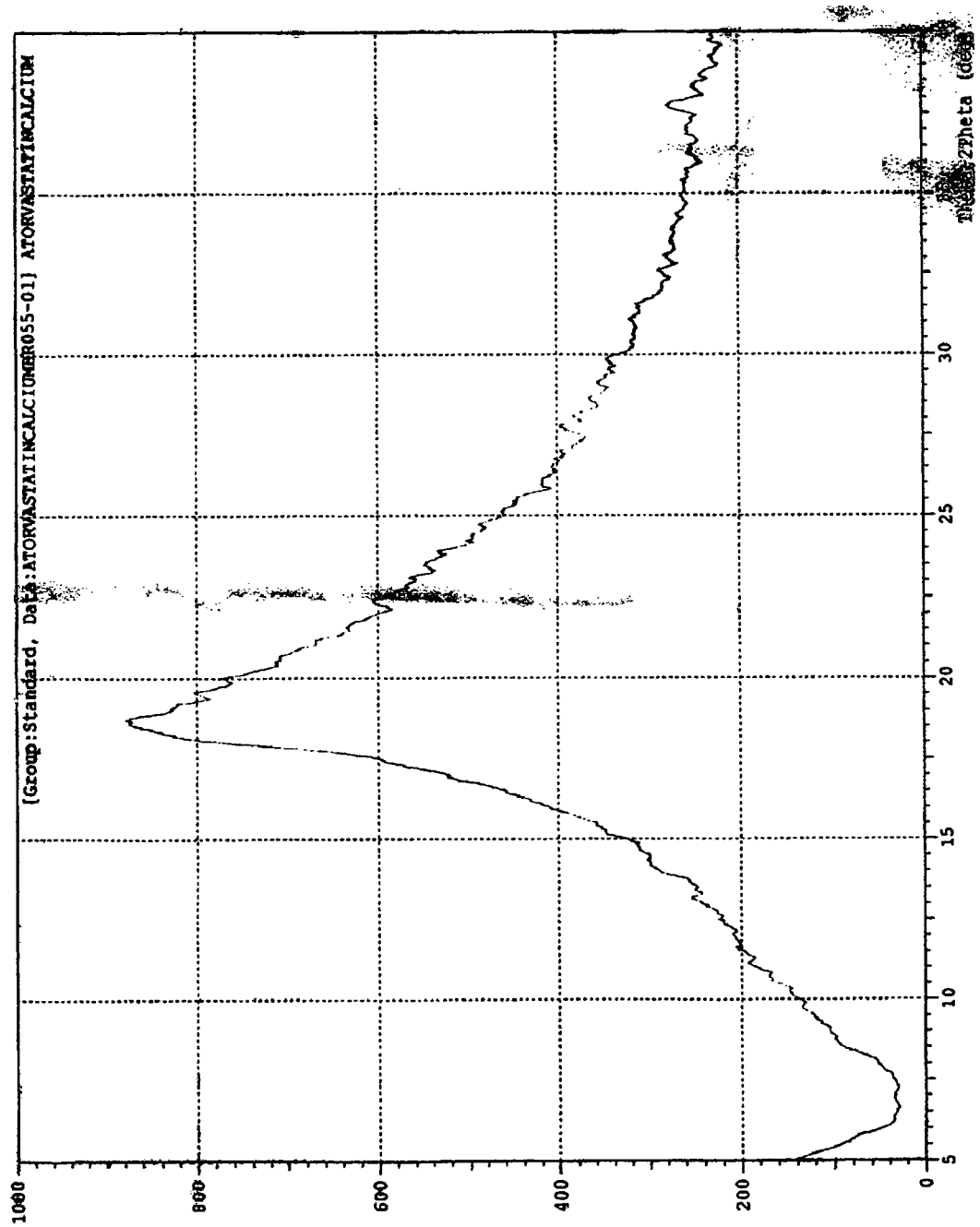

FIG. 3. demonstrates the amorphous form of the product of the formula of FIG. 2.

Figure 4:
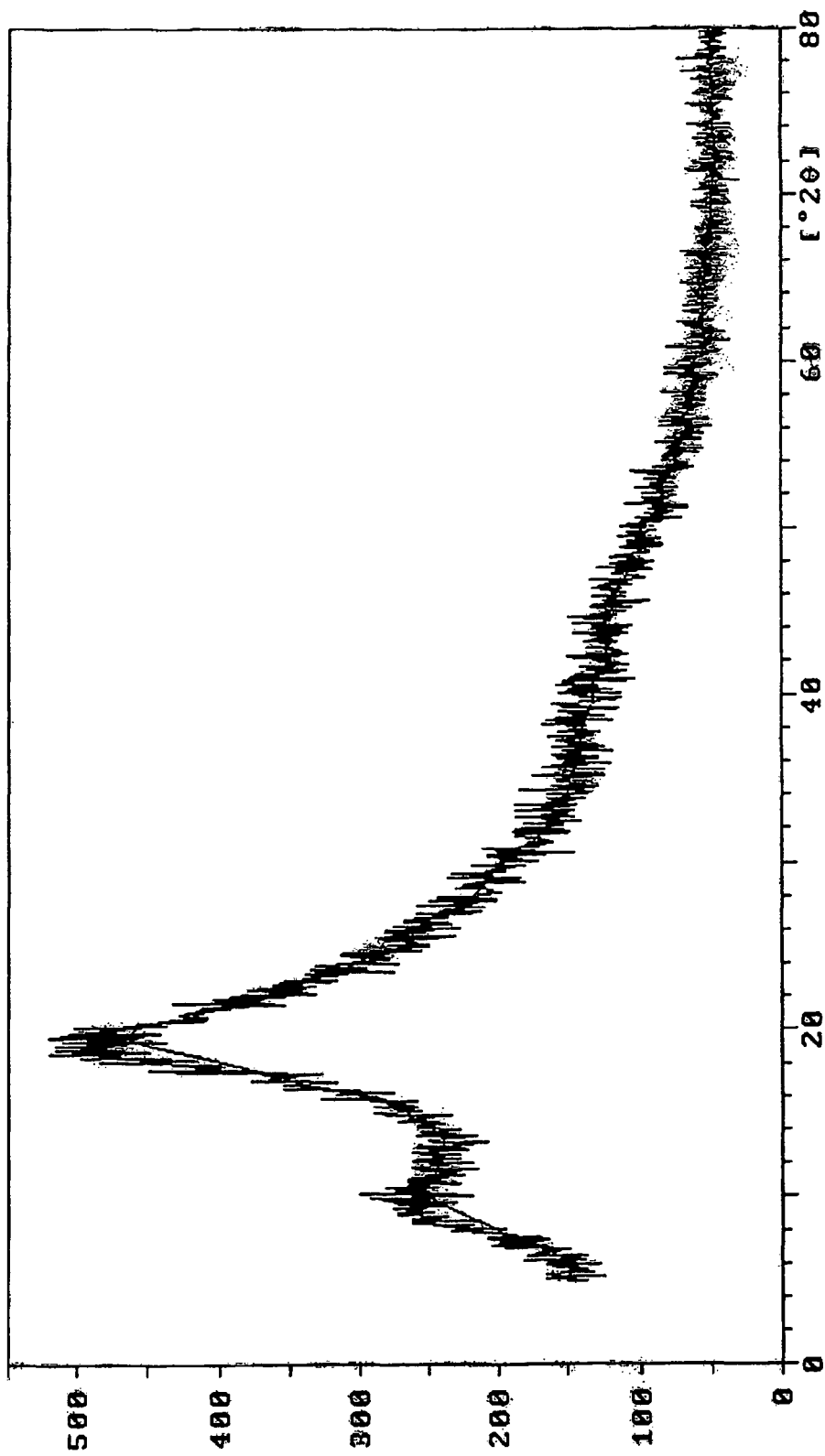

FIG. 4. demonstrates the amorphous form of the product of the formula of FIG. 2.

In the prior art the compound of formula of FIG. 1 is disclosed in U.S. Pat. No. 4,681,893, while U.S. Pat. No. 5,273,995 discloses the enantiomers having the R-form of the ring-opened acid i.e. of formula of FIG. 2. U.S. Pat. Nos. 5,003,080; 5,097,045; 5,103,024; 5,124,482; 5,149,837; 5,155,251; 5,216,174; 5,248,793; 5,280,132; 5,342,952; 5,007,080; describes the various processes and key intermediates for preparing atorvastatin calcium. All these processes give mixtures of crystalline and amorphous forms.

PCT application WO 97/033959 discloses various crystalline forms of atorvastatin calcium salts.

PCT application WO 97/03960 discloses a method for the production of amorphous atorvastatin calcium by dissolving its crystalline form in a non-hydroxy solvent like tetrahydrofuran or mixture of toluene and tetrahydrofuran and after removal of solvents gives amorphous atorvastatin calcium. The process has disadvantage as the solvents are removed by vacuum drying or spray drying at 90° C. and under high vacuum which leads to degradation of the product at such high temperature. The process is also inconvenient to carry out at commercial scale. PCT application WO 00/71116 describes the process of preparing amorphous atorvastatin calcium by dissolving its crystalline form in non-hydroxyl solvent like tetrahydrofuran and then adding antisolvent like non-polar hydrocarbon i.e. hexane, cyclohexane, heptane. The product is isolated by filtration. This process has the disadvantages as it prepares amorphous atorvastatin calcium by taking solvents which are difficult to remove in drying thus giving high limits of residual solvents.

The object of this invention is to prepare amorphous atorvastatin calcium without isolating crystalline atorvastatin calcium. The advantage of the invention is that the process is suitable for commercial scale production, high yield and purity, very low value of residual solvents, fast filtration and great degree of reproducibility of making amorphous atorvastatin calcium.

Accordingly, this invention provides an improved process for the preparation of amorphous atorvastatin calcium, [R—(R*,R*)]-2-(4-fluorophenyl)-β,δ-dihydroxy-5-(1-methylethyl)-phenyl-4-[(phenylamino)carbonyl]-1H-pyrrole-1-heptanoic acid calcium salt (2:1) having formula of FIG. 2, which is characterized in that its preparation is carried out directly from a concentrated organic solvent of the reaction mixture of (2R-trans)-5-(4-fluorophenyl)-2-(1-methyl ethyl)-N,4-diphenyl-1-[2-(tetrahydro-4-hydroxy-6-oxo-2H-pyran-2-yl)ethyl]-1-H-pyrrole-3-carboxamide of formula of FIG. 1 with aqueous solution of alkali or alkaline earth metal hydroxide, with an organic anti-solvent of group comprising aliphatic ether or non-polar hydrocarbons.

According to another aspect of the invention, the preparation of amorphous atorvastatin calcium, [R—(R*,R*)]-2-(4-fluorophenyl)-β,δ-dihydroxy-5-(1-methylethyl)-phenyl-4 [(phenyl amino)carbonyl]-1H-pyrrole-1-heptanoic acid calcium salt (2:1) having formula of FIG. 2, which is characterized in that its preparation is carried out from a concentrated organic solvent of the reaction mixture of crystalline form of atorvastatin calcium (2:1) salt of formula of FIG. 2 with an organic anti-solvent of group comprising aliphatic ether or non-polar hydrocarbons.

According to an aspect of the invention, the alkali and alkaline metal hydroxide used are calcium hydroxide or sodium hydroxide.

According to another aspect of the invention the reaction mixture is dissolved in DM water and extracted with an organic solvent in a quantity of 1-100 times of compound of formula of FIG. 1 or upto 10 times thereof.

According to further aspect of the invention, the organic solvent used for extraction are halogenated aliphatic hydrocarbons such as methylene chloride, ethylene dichloride, chloroform, aliphatic esters such as ethyl acetate, n-butyl acetate or aromatic hydrocarbon such as toluene. The organic solvent used is 1-100 times in volume and the reaction mixture extract is concentrated upto a volume of 1-50 times. The thus concentrated reaction mixture extract is added dropwise for precipitation to an anti-solvent like di-isopropyl ether, diethyl ether or a non-polar hydrocarbon like petroleum ether. The organic solvent used for extraction of the reaction mixtures is 30-40 times in volume and the solvent extract obtained is concentrated by volume of 5-10 times, which is added to upto 20-30 times of the anti-solvent dropwise to precipitate the amorphous salt. The precipitation with the anti-solvent is carried out at a temperature of −20 to 60° C. or between −5 to 5° C. and the amorphous atorvastatin calcium salt is obtained by filtration thereof.

The process for the preparation of the amorphous atorvastatin calcium and hydrates thus consists of:

Process 1:
 a) Compound of formula of FIG. 1 is dissolved in an organic solvent like aliphatic straight chain or branched alcohol, cyclic ether, aliphatic ketone or aliphatic amide.
 b) Addition of aqueous solution of alkali metal and alkaline earth metal hydroxide.
 c) Stirring till disappearance of compound of formula of FIG. 1 (TLC/HPLC monitoring).
 d) Addition of DM water.
 e) Extraction of compound of formula of FIG. 2 with organic solvent from the group comprising halogenated aliphatic hydrocarbons, aliphatic ester or aromatic hydrocarbons.
 f) Concentrating of organic solvent containing compound of formula of FIG. 2.
 g) Addition of concentrated mass to a anti-solvent from the group comprising aliphatic ether or non-polar hydrocarbons, and
 h) Filtering the product to afford amorphous atorvastatin calcium salt (2:1).

Process 2:

a) Crystalline form of compound of formula of FIG. 2 is dissolved in an organic solvent from the group comprising halogenated aliphatic hydrocarbons, aliphatic ester or aromatic hydrocarbons.

b) Concentrating of organic solvent containing compound of formula of FIG. 2.

c) Addition of concentrated mass to a anti-solvent from the group comprising aliphatic ether or non-polar hydrocarbons, and d) Filtering the product to afford amorphous atorvastatin calcium salt (2:1).

The organic solvents used in the dissolution are methanol, ethanol, isopropyl alcohol, tetrahydrofuran, 1,4-dioxan,N,N-dimethyl formamide, N,N-dimethyl acetamide and the like. The alkali metal and alkaline earth metal hydroxide used for hydrolysis are calcium hydroxide, sodium hydroxide. The solvent ratio to the compound of formula of FIG. 1 is 1:50, preferably 5 times. The temperature during the dissolution is −10 to 60° C., preferably 25 to 30° C. In the hydrolysis with sodium hydroxide, aqueous solution of calcium acetate or calcium chloride has to be added in order to form calcium salt. The preferably used base is calcium hydroxide. The mole ratio of base used is 0.5-5 mole against compound of formula of FIG. 1, preferably 1.0 mole. The hydrolysis is carried out at 0 to 60° C., preferably at 40 to 45° C. DM water added for dilution is 1-100 times of the compound of formula of FIG. 1, preferably 10 times. The organic solvents used for extraction are methylene chloride, ethylene dichloride, chloroform, ethyl acetate, n-butyl acetate or toluene, preferably methylene chloride in the ratio of 1-100 times of compound of formula of FIG. 1 or compound of formula of FIG. 2 (crystalline form), preferably 30-40 times, most preferably 35 times. The organic layer is concentrated to volume of 1-50 times of the compound of formula of FIG. 1 or compound of formula of FIG. 2 (crystalline form), preferably 5-10 times, most preferably 8 times. The concentrated mass is added under stirring to a anti-solvent like di-isopropyl ether, di-ethyl ether, petroleum ether in the ratio of 1-100 times of compound of formula of FIG. 1 or compound of formula of FIG. 2 (crystalline form), preferably 25 times.

The concentrated mass is added under stirring to a anti-solvent like di-isopropyl ether, di-ethyl ether, petroleum ether in the ratio of 1-100 times of compound of formula of FIG. 1, preferably 25 times. The temperature during precipitation is −20 to 60° C., preferably −5 to 5° C., most preferably 0 to 2° C. Generally, the product can be isolated by any standard method known in the art such as by filtration, centrifugation or decantation. Typically this product is recovered by filtration. The filtration is very fast and smooth. The semi-dried material is dried in a vacuum tray drier at 20-60° C., most preferably 45-50° C. The time of drying is about 4 to 24 hours, preferably is 12 hours.

Amorphous atorvastatin calcium prepared according to the process of the invention may be characterized by its X-ray powder diffraction pattern of FIG. 3 and FIG. 4. X-ray powder diffraction shows no peaks thus demonstrating the amorphous nature of the product. The FIGS. 3 and 4 are diffractograms of atorvastatin calcium. The horizontal axis represents 2θ and the vertical axis corresponds to peak intensity.

The invention is further illustrated by the processes of the following examples which do not limit the effective scope of the claims.

EXAMPLE I

[R—(R\*,R\*)]-2-(4-Fluorophenyl)-β,δ-dihydroxy-5-(1-methylethyl)-3-phenyl-4-[(phenyl amino)carbonyl]-1H-pyrrole-1-heptanoic acid calcium salt (2:1)

Method A: (2R-trans)-5-(4-Fluorophenyl)-2-(1-methylethyl)-N,4-diphenyl-1-[2(tetrahydro-4-hydroxy-6-oxo-2H-pyran-2-yl)ethyl]-1H-pyrrole-3-carboxamide (compd. of formula-I) (100.0 gms, 0.185 mole) was dissolved in tetrahydrofuran (500 ml) under stirring at 25-30° C. To this was added calcium hydroxide (13.68 gms, 0.185 mole) suspended in DM-water (100 ml). The reaction mass was stirred at 45-50° C. till disappearance of compd. of formula-I on TLC (time 2 hrs.). DM-water (1.0 lt) was added to the reaction mass under stirring. Methylene chloride (3.0 lt) was added and stirred for 30 min. at 30-32° C. The layers were separated and upper aqueous layer was re-extracted with methylene chloride (500 ml). Both the organic layer was mixed and concentrated up to volume (800 ml) at 40-42° C. at atmospheric pressure. The concentrated organic layer was fine filtered and added drop wise into pre-cooled di-isopropyl ether (0-2° C., 2.5 lts.) under stirring in 45 minutes. After the complete addition, the reaction mass was farther stirred for 30 minutes at the same temperature. The product was filtered under suction and semi-dried material was dried at 45-50° C. in a vacuum drier.

Atorvastatin Calcium (100.0 gm, 93.6%) in an amorphous form was obtained having the following analysis:

| | |
|---|---|
| Relative purity (HPLC) | 99.3% |
| Assay (OAB, HPLC) | 98.99% |
| Calcium content | 3.39% |
| FTIR (KBr) | 3407, 2964, 2930, 1665, 1595, 1561, 1527, 1506, 1435, 1312, 1223, 1156, 1109, 842, 752 cm$^{-1}$ |
| Residual solvent: | |
| Methanol | <0.05% |
| Tetarhydrofuran | <0.05% |
| Methylene chloride | <0.05% |
| Di-Isopropyl ether | <0.1% |

XRD: FIG. 3 demonstrate the amorphous from of the product.

Method B: (2R-trans)-5-(4-Fluorophenyl)-2-(1-methylethyl)-N,4-diphenyl-1-[2-(tetrahydro-4-hydroxy-6-oxo-2H-pyran-2-yl )ethyl]-1H-pyrrole-3-carboxamide (compound of formula I)(100.0 gm,0.185 mole) was dissolved in methanol (500 ml) under stirring at 25-30° C. To this was added sodium hydroxide (8 gm, 0.20 mole) in DM-water (80 ml). The reaction mass was stirred at 45-50° C. till disappearance of compound of formula I on TLC (Time: 2 hrs). DM-water (1.0 Lt) was added to the reaction mass under stirring. Calcium acetate monohydrate (16.0 g, 0.091 mole) in DM-water (1.0 lt.) was added at 30-32° C. Methylene chloride (3.0 lt) was added and stirred for 30 min. at 30-32° C. The layers were separated and upper aqueous layer was re-extracted with methylene chloride (500 ml). Both the organic layer was mixed and concentrated up to volume (800 ml) at 40-42° C. at atmospheric pressure.

The concentrated organic layer was fine filtered and added dropwise into pre-cooled di-isopropyl ether (0-2° C., 2.5 lt.) under stirring in 45 minutes. After the complete addition, the reaction mass was further stirred for 30 minutes at the same temperature. The product was filtered under suction and material was dried at 45-50° C. in a vacuum drier for 12 hours. Atorvastain calcium (95.0 gm, 88.92%) in an amorphous form was obtained having the following analysis.

| | |
|---|---|
| Relative purity (HPLC) | 99.3% |
| Assay (OAB, HPLC) | 99.0% |
| Calcium Content | 3.10% |
| FTIR (KBr) | 3410, 2960, 2928, 1664, 1595, 1561, 1527, 1509, 1436, 1312, 1224, 1156, 1109, 843, 752 cm$^{-1}$. |
| Residual solvent: | |
| Methanol | <0.05% |
| Tetrahydrofuran | <0.05% |
| Methylene Chloride | <0.05% |
| Di-isopropyl ether | <0.1% |

XRD: FIG. 4 demonstrate the amorphous form of the product.

Example II

[R—(R*,R*)]-2-(4-Fluorophenyl)-β,δ-dihydroxy-5-(1-methylethyl)-3-phenyl-4[(phenyl amino)carbonyl]-1H-pyrrole-1-heptanoic acid calcium salt (2:1)

Method: Crystalline atorvastatin calcium (2:1) salt (100.0 gms, 0.173 mole) was dissolved in methylene chloride (3.0 lt) and stirred for 30 min. at 36-38° C. and concentrated up to volume (800 ml) at atmospheric pressure. The concentrated organic layer was fine filtered and added drop wise into pre-cooled di-isopropyl ether (0-2° C., 2.5 lts.) under stirring in 45 minutes. After the complete addition, the reaction mass was farther stirred for 30 minutes at the same temperature. The product was filtered under suction and semi-dried material was dried at 45-50° C. in a vacuum drier. Atorvastain calcium (90.0 gm, 90.0%) in an amorphous form was obtained having the following analysis.

| | |
|---|---|
| Relative purity (HPLC) | 98.94% |
| Calcium Content | 3.30% |
| FTIR (KBr) | 3408, 2963, 2930, 1664, 1594, 1560, 1527, 1508, 1435, 1312, 1223, 1156, 1109, 1076, 1031, 842, 752 cm$^{-1}$. |
| Residual solvent: | |
| Methanol | <0.05% |
| Tetrahydrofuran | <0.05% |
| Methylene Chloride | <0.05% |
| Di-isopropyl ether | <0.1% |

The process of example I and II was repeated by using different solvent as claimed giving amorphous atorvastatin calcium.

While the present invention has been described in terms of its specific embodiments, certain modifications and equivalents will be apparent to these skilled in the art and are intended to be included within the scope of the present invention.

We claim:

1. An improved process for the preparation of amorphous atorvastatin calcium, [R—(R*,R*)]-2-(4-Fluorophenyl)-β,δ-dihydroxy-5-(1-methylethyl)-3-phenyl-4-[(phenylamino) carbonyl]1H-pyrrole-1-heptanoic acid calcium salt (2:1) having formula

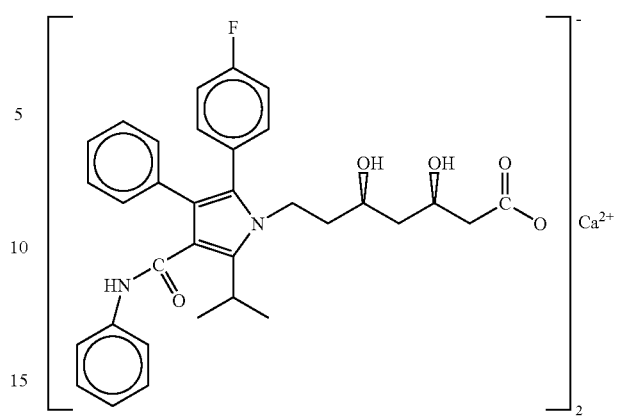

comprising:
(a) obtaining a reaction mixture of (2R-trans)-5-(4-fluorophenyl)-2-( 1-methyl ethyl)-N,4-diphenyl-1-[2-(tetrahydro-4-hydroxy-6-oxo-2H-pyran-2-yl)ethyl]-1-H-pyrrole-3-carboxamide of formula:

and an aqueous solution of alkali or alkaline earth metal hydroxide;
(b) extracting reaction product of step (a) in an organic solvent that is methylene chloride;
(c) adding an anti-solvent that is diisopropyl ether to the extracted product of step (b); and
(d) isolating the amorphous atorvastatin calcium after step (c) followed by drying at 45-50° C.

2. An improved process for the preparation of amorphous atorvastatin calcium, [R—(R*,R*)]-2-(4-Fluorophenyl)-β,δ-dihydroxy-5-(1-methylethyl)-3-phenyl-4-[(phenyl amino) carbonyl]1H-pyrrole-1-heptanoic acid calcium salt (2:1) having formula, comprising:
(a) dissolving a crystalline form of atorvastatin calcium (2:1) having formula

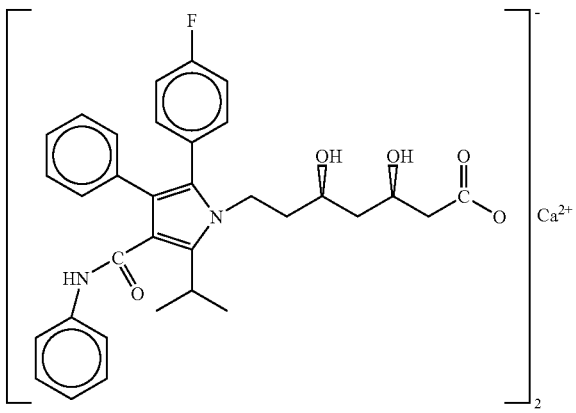

in methylene chloride:
(b) adding diisopropyl ether to the resulting solution of step (a); and
(c) isolating the amorphous atorvastatin calcium after step (b) followed by drying at 45-50° C.

3. The process of claim 1 or 2, wherein an amount of methylene chloride used is 10-35 times by volume with respect to the amount of (2R-trans)-5-(4-fluorophenyl)-2-(1-methyl ethyl)-N,4-diphenyl- 1-[2(tetrahydro-4-hydroxy-6-oxo-2H-pyran-2-yl)ethyl]-1-H-pyrrole-3-carboxamide or the crystalline form.

4. The process of claim 1 or 2, wherein the diisopropyl ether used is up to 15-25 times by volume with respect to the amount of(2R-trans)-5-(4-fluorophenyl)-2-(1-methyl ethyl)-N,4-diphenyl-1-[2-(tetrahydro-4-hydroxy-6-oxo-2H-pyran-2-yl)ethyl]-1-H-pyrrole-3-carboxamide or the crystalline form.

* * * * *